(12) United States Patent
Krumme

(10) Patent No.: US 6,319,237 B1
(45) Date of Patent: Nov. 20, 2001

(54) URINARY SPHINCTER CONTROL DEVICE

(75) Inventor: John F. Krumme, Tahoe City, CA (US)

(73) Assignee: ICD Labs, Inc., Palo Alto, CA (US)

( * ) Notice: Subject to any disclaimer, the term of this patent is extended or adjusted under 35 U.S.C. 154(b) by 0 days.

(21) Appl. No.: 09/298,392

(22) Filed: Apr. 23, 1999

(51) Int. Cl.[7] ................................................ A61M 5/14
(52) U.S. Cl. ................... 604/256; 128/887; 128/DIG. 25
(58) Field of Search ..................... 604/256; 600/29–32; 623/14; 128/DIG. 25, 885, 887

(56) References Cited

U.S. PATENT DOCUMENTS

| | | | |
|---|---|---|---|
| 4,399,809 | * 8/1983 | Baro et al. | 128/DIG. 25 |
| 4,428,365 | * 1/1984 | Hakky | 128/DIG. 25 |
| 4,503,569 | 3/1985 | Dotter | 606/191 |
| 4,556,050 | 12/1985 | Hodgson et al. | 600/30 |
| 5,147,370 | 9/1992 | McNamara et al. | 623/1 |
| 5,354,309 | 10/1994 | Schnepp-Pesch et al. | 623/11 |
| 5,466,242 | 11/1995 | Mori | 623/1 |
| 5,514,178 | 5/1996 | Torchio | 606/191 |
| 5,540,713 | 7/1996 | Schnepp-Pesch et al. | 623/11 |
| 5,554,181 | 9/1996 | Das | 606/194 |
| 5,601,593 | 2/1997 | Freitag | 623/1 |
| 5,893,826 | * 4/1999 | Salama | 600/31 |

* cited by examiner

Primary Examiner—Richard K. Seidel
Assistant Examiner—Kevin C. Sirmons
(74) Attorney, Agent, or Firm—Madson & Metcalf

(57) ABSTRACT

A urinary sphincter control device for application to a urethra to control flow of fluid through the urethra, comprises a cuff which can be fitted around the urethra. The cuff comprises a plurality of chambers which extend generally parallel to the axis of the cuff, and which can be inflated by supply of pressurised control fluid thereto. Inflation of the chambers causing the configuration of the cuff to change so as to alter the resistance that is provided by the cuff to flow of fluid along the urethra.

16 Claims, 3 Drawing Sheets

URINARY SPHINCTER CONTROL DEVICE

BACKGROUND TO THE INVENTION

This invention relates to a urinary sphincter control device for application to a urethra to control flow of fluid through the urethra.

Known devices for controlling incontinence comprise a cuff which can be fitted around a patient's urethra. The cuff comprises at least one chamber which extends around the urethra. A pressurised control fluid can be supplied to the cuff to inflate it, causing the cuff to exert compressive pressure onto the urethra so that flow of fluid along the urethra is prevented. The fluid that is used in such devices might be for example a saline solution. The device will generally include a reservoir for the fluid, and a pump by which pressurised fluid can be supplied to the cuff and withdrawn from the cuff. Known devices include an elastic balloon reservoir by which the pressure of the fluid in the cuff can be controlled within predetermined limits.

A cuff which extends around the urethra has been found to close a urethra satisfactorily against flow of fluid. However, the cuff can also restrict the flow of blood along the urethra, leading to tissue damage and the subsequent need to remove the device from the patient.

SUMMARY OF THE INVENTION

The present invention provides a urinary sphincter control device in which the cuff comprises a plurality of chambers which are discontinuous around the vessel so that blood is able to flow along the vessel in its wall even when the vessel is closed against fluid flow, which can be inflated to cause the configuration of the cuff to change so as to alter the resistance that is provided by the cuff to flow of fluid along the urethra.

The device of the invention has the advantage that it is able to close a urethra against flow of fluid through its bore by closing the vessel transversely. However, the chambers by which the closing force is applied to the vessel are discontinuous around the vessel so that blood is able to flow along the vessel in its wall even when the vessel is closed against fluid flow. The chambers might for example extend generally parallel to the axis of the cuff. The device of the invention can therefore be more comfortable for a patient to use, with reduced likelihood of urethra tissue damage than with existing devices. As a consequence, the device of the invention minimises the need for surgical procedures after implantation to address problems of tissue damage following use of the device.

The advantage that is provided by the present invention in terms of reduced resistance to flow of blood in the urethra arises from the fact that the chambers in the cuff by which force can be applied to the urethra extend generally parallel to the axis of the cuff so as to be aligned with the blood flow in the urethra. In some cases, the orientation of the chambers might be such that they do not extend parallel to the cuff axis provided that the angle between the axes of the chambers and the direction of blood flow is small. Preferably the angle between the axis of the cuff and the axis of the chambers is less than about 20°, more preferably less than about 10°. It will generally be preferred for the chambers to be orientated as close as possible to the cuff axis.

The device of the invention can be arranged so that flow of fluid along the urethra is restricted by the cuff when it is in its inflated configuration. Flow of fluid along the urethra is then allowed by deflation of the cuff, with pressure of fluid within the urethra enhancing the cuff deflation. A device which operates in this way can include a pump for changing the pressure of the control fluid within the cuff, and preferably also means for controlling the pressure of the control fluid so that (a) it is sufficient to close the urethra against fluid flow, but (b) not so great as to cause damage to the cuff or to the patient's tissue. Devices for changing and for controlling the pressure in the cuff in this way are known.

It will be preferred for the device to be arranged so that flow of fluid along the urethra is restricted by the cuff when it is in its uninflated configuration, and in which the effective internal perimeter (which will be a circumference when the cross-section of the device is circular) dimension of the cuff is increased when it is in its inflated configuration so that the pressure imposed by the cuff on the urethra is reduced and so that the urethra is opened to flow of fluid therethrough. Inflation of the chambers of the device increases the internal transverse dimension of the cuff, and can therefore reduce the pressure exerted by the cuff on the urethra. In this arrangement, the maximum force that is imposed on the urethra can be pre-determined. The force that is imposed can then be controlled to suit the requirements of a particular patient by controlling the pressure of fluid that is supplied to the cuff. It is an advantage of this arrangement that the application of the closure force to the urethra can be adjusted externally by controlling the pressure and volume of fluid in the cuff. The device therefore enables the closure force imposed on the urethra to be adjusted after implantation of the device.

Preferably, the device includes, in at least one of the chambers, an element for biassing the configuration of the chamber towards the uninflated configuration. The element can be designed to provide a desired closing force to a urethra on which the cuff is to be used when it operates. Preferred biassing elements are formed from shape memory alloys, especially which exhibit enhanced elastic properties. Articles formed from shape memory alloys can exhibit shape memory properties associated with transformations between martensite and austenite phases of the alloys. These properties include thermally induced changes in configuration in which an article is first deformed from a heat-stable configuration to a heat-unstable configuration while the alloy is in its martensite phase. Subsequent exposure to increased temperature results in a change in configuration from the heat-unstable configuration towards the original heat-stable configuration as the alloy reverts from its martensite phase to its austenite phase.

Shape memory alloys can exhibit enhanced elastic properties compared with materials which do not exhibit martensite-austenite transformations and it is these properties that make the alloys attractive for use in the device of the present invention. The nature of the enhanced elastic transformations of shape memory alloys is discussed in "Engineering Aspects of Shape Memory Alloys", T W Duerig et al, on page 370, Butterworth-Heinemann (1990). Subject matter disclosed in that document is incorporated in this specification by this reference to the document. A principal transformation of shape memory alloys involves an initial increase in strain approximately linearly with stress. This behaviour is sometimes referred to as non-linear superelasticity. It is reversible, and corresponds to conventional elastic deformation. Subsequent increases in strain are accompanied by little or no increase in stress over a limited range of strain to the end of the "loading plateau". The loading plateau stress is defined by the inflection point on the stress/strain graph. Subsequent increases in strain are accompanied by increases in stress. On unloading, there is a decline in stress with reducing strain to the start of the "unloading plateau" evidenced by the existence of an inflection point along which stress changes little with reducing strain. At the end of the unloading plateau, stress reduces with reducing strain. The unloading plateau stress is also defined by the inflection point on the stress/strain graph. Any residual strain after unloading to zero stress represents the permanent set of the sample. Characteristics of this deformation, the loading plateau, the unloading plateau, the elastic modulus, the plateau length and the permanent set (defined with respect to a specific total deformation) are established, and are defined in, for example, "Engineering Aspects of Shape Memory Alloys", on page 376.

The thermally induced transformation from the austenite phase to the martensite phase on cooling begins at a temperature known as the $M_s$ temperature, and is completed at a temperature known as the $M_f$ temperature. The transformation of the martensite phase to the austenite phase upon heating begins at a temperature known as the $A_s$ temperature and is complete at a temperature known as the $A_f$ temperature. The application of a load tends to favour, or to stabilise the martensite phase. Non-linear superelastic properties are exhibited when the austenitic phase is stable in the absence of a load, yet the martensitic phase can temporarily become the stable phase when a load of sufficient magnitude is introduced. Thus these properties require that one maintains the material temperature slightly above the $A_f$ temperature. The temperature above which all traces of superelasticity are lost is called the $M_d$ temperature.

A preferred way in which non-linear superelastic properties can be introduced in a shape memory alloy involves cold working the alloy by one of several deformation methods, for example, swaging, drawing, pressing, stretching or bending. The cold working step is followed by an annealing step at a temperature less than the recrystallization temperature of the alloy, for a time sufficient to cause dislocations to rearrange, combine and align themselves (so-called "recovery" processes).

Alloys from which the biassing element can be made include nickel-titanium based alloys, especially Ni—Ti binary alloys such as those in which the nickel content is at least about 50 at. %, preferably at least about 50.5 at. %. The nickel content will usefully be less than about 54 at. %, preferably less than about 52 at. %. The method can also be performed on other Ni—Ti based alloys, including alloys with ternary and quaternary additions. Examples of elements that can be incorporated in the alloy include Fe, Co, Cr, Al, Cu and V. Added elements can be present in amounts up to about 10 at. %, preferably up to about 5 at. %.

Examples of particularly preferred alloys include alloys which consist of 55.8 at. % Ni and 44.2 at. % Ti, and 50.5 at. % Ni and 49.5 at. % Ti respectively (not including impurities).

A shape memory alloy that is used for the biassing element should preferably be selected so that its $A_f$ temperature is at least about 15° C., preferably at least about 20° C. Preferably, the $A_f$ temperature is not more than about 30° C., more preferably not more than about 25° C.

In another aspect, the present invention provides a urinary sphincter control device for application to a urethra to control flow along the urethra, which comprises (a) a cuff which can be fitted around the urethra and which can be inflated to cause the configuration of the device to change between an uninflated configuration in which flow of fluid along the urethra is restricted and an inflated configuration in which fluid is able to flow along the urethra, and (b) an element for biassing the device towards the uninflated configuration, the element being formed from a shape memory alloy which has been treated so that it exhibits enhanced elastic properties at body temperature, allowing it to be deformed by inflation of the cuff and to recover elastically when the cuff deflates.

The use of a shape memory biassing element in the device of the present invention has the advantage that the force that is applied by the device when acting against the urethra to close it against fluid flow can be controlled. The control is available through design of the biassing element. For example, the shape of the biassing element (including its thickness) as well as the material from which it is made can be changed to provide suitable properties.

Control is also made possible by selection of the conditions for the treatment of the alloy by which it is given its enhanced elastic properties: for example, the treatment can affect the stress on the loading and unloading plateaus discussed above. The design of the biassing element can affect the range of strains over which the biassing element can be deformed. For example, the characteristic stresses of the loading and loading plateaus can be changed by changing the degree of work hardening to which the alloy is exposed.

In the device of the invention with the shape memory biassing means, it is preferred that the cuff comprises a plurality of chambers which can be inflated by supply of pressurised control fluid thereto to cause the configuration of the cuff to change so as to alter the resistance that is provided by the cuff to flow of fluid along the urethra. Preferably, the biassing elements are provided in at least one of the chambers.

Preferably, the biassing element has a generally tubular configuration with the axis of the tube extending generally parallel to the axis of the chamber in which it is located, the biassing element having a generally flattened cross-section when viewed along the axis of the chamber in its uninflated configuration, and in which supply of control fluid to the chamber causes its cross-section to become more rounded. The tube need not be closed when viewed in cross-section. Preferably, the biassing element is formed as a tube with a closed cross-section, for example by extrusion or by forming from a sheet.

A generally tubular biassing element can have one or more slots formed in its wall. Slots can increase the ability of the element to flex transversely, making it more comfortable for the user. They can also affect the forces that are imposed by the device on a patient's urethra. The slots will extend in a plane that is non-parallel to the axis of the tube, especially close to perpendicular to the said axis. When the tube has a circular cross-section, the slots will extend generally circumferentially around the tube. The slots can extend around substantially the entire periphery of the element so that the element has the configuration of a plurality of rings that are interconnected by fingers spaced apart around the rings. An element with such a configuration can be made by controlled cutting a tube of the shape memory alloy for example using a YAG laser cutter device, preferably operating in an environment of an oxygen/argon mixture.

A biassing element which is generally flattened when the chamber is uninflated can be arranged so that the axis of the tube extends along the chamber, and so that one of the edges of the element when flattened is directed towards the centre of the cuff, that is towards the urethra. The edge of the biassing element pointing towards the urethra tends to give the device a reduced internal perimeter dimension so that the urethra is constricted by the device.

Preferably, the cuff will comprise a plurality of inflatable chambers. For example, for many applications, the cuff will comprise at least eight chambers, preferably at least ten chambers, especially at least twelve chambers. Preferably, at least half, especially all, of the chambers contain biassing elements. Preferably, the chambers are provided in at least one array. The array can extend around substantially the entire periphery of the cuff. It can however be preferred for the array to extend around part only of the periphery of the cuff. There can be more than one array, and such arrays can extend around spaced apart regions of the cuff. Often, when there is more than one array the arrays can be arranged substantially equally spaced apart around the cuff.

The use of a cuff with a plurality of inflatable chambers provides flexibility in the application of force to a urethra; the distribution of the force around the urethra can be selected by selection of the number and arrangement of the chambers that are made to change configuration, by the application of pressure or by a biassing element or both. When the device is arranged so that flow of fluid along the urethra is restricted by the cuff when it is in its uninflated configuration, and in which the effective internal perimeter dimension of the cuff is increased when it is in its inflated configuration so that the pressure imposed by the cuff on the urethra is reduced and the urethra is opened to fluid flow, each of the chambers through which force is applied to the urethra will preferably be provided with a biassing element, and each of those chambers will generally be capable of being inflated to open the urethra to fluid flow.

When multiple adjacent chambers are to be inflated with control fluid, they can be arranged for the fluid to flow into them in series. This has the advantage that the connection of the device to the supply of the control fluid is simplified. A passage for control fluid to flow between chambers in the cuff can include openings in the biassing element in each chamber to minimise obstructions to flow of the fluid through the cuff.

The device of the invention can include an actuator by which the pressure in the cuff can be adjusted. The actuator will then be in fluid communication with the cuff. The actuator should preferably include means for applying an increased pressure in the control fluid supplied to the cuff. An appropriate component might include for example a piston and cylinder arrangement. The actuator can include a latch for retaining the actuator in such a configuration that the increased pressure in the cuff is retained for as long as required for adequate flow of fluid in the urethra. Preferably, the actuator is such that the action required to open the cuff for fluid flow requires one or two strokes, especially by a single finger.

The use of a biassing element to provide or to enhance the closing force on the urethra gives rise to the advantage over devices in which a closing force is applied hydraulically that the number of components of the device is kept to a minimum without compromising the control over the closing force applied to the urethra. This keeps the device of the invention small, and also simplifies the surgical procedure involved in implantation. The fact that the device of the invention is relatively small also makes possible its use in females as well as males: the female anatomy places more strict requirements on the size of a urinary sphincter control device than does the male anatomy. An actuator component of the device can be implanted in the lower abdomen region. The actuator will generally be accessible externally, especially by manipulation through the skin using the patient's finger tip. It can also be preferred for the level of control fluid in the reservoir to be capable of being adjusted from outside the reservoir; for example, it can be preferred for the reservoir to be sealed by a septum which can be penetrated by a hypodermic needle with an associated syringe, through which fluid can be added to the reservoir or withdrawn from it.

The device of the invention should be capable of reducing the size of a urethra so that it can provide a seal against fluid flow to withstand a pressure of at least about 6.5 kPa, preferably at least about 7.5 kPa, for example about 9.0 kPa. The device should be capable of allowing relatively unimpeded flow of fluid through the urethra when the device is in its open configuration. The internal transverse dimension or effective diameter (which will be the diameter when the device has a circular cross-section) of the device will generally be at least about 5 mm, preferably at least about 10 mm. The internal transverse dimension will often be less than about 25 mm, preferably less than about 20 mm. For example, a large male patient might require an effective diameter of the device of about 15 to 25 mm, while a female or child might require a smaller cuff in the range 5 to 15 mm.

The length of the cuff, and preferably also of the chambers when they are oriented so that they extend parallel to the axis of the cuff, will often be at least about 10 mm, preferably at least about 15 mm. The length will generally be not more than about 130 mm and preferably less than about 20 mm.

Suitable materials for the cuff include medical grade silicone polymers, polyolefins, polyurethanes and halogenated olefin polymers such as polytetrafluoroethylene. Conventional techniques for making polymer components can be used for forming the cuff including for example extrusion and moulding.

The configuration and size of the biassing element will be selected according to the design of the cuff. Preferably, the length of the external peripheral dimension of the biassing element (when viewed in cross-section) will be only a little less than the length of the internal peripheral dimension of the chamber in which the biassing element is located, for example not more than about 25% less, more preferably not more than about 20% less, especially not more than about 15% less. The length of the external peripheral dimension of the biassing element can suitably be less than about 8 mm, preferably less than about 5 mm.

INTRODUCTION TO THE DRAWINGS

DESCRIPTION OF PREFERRED EMBODIMENTS

Figure 1:
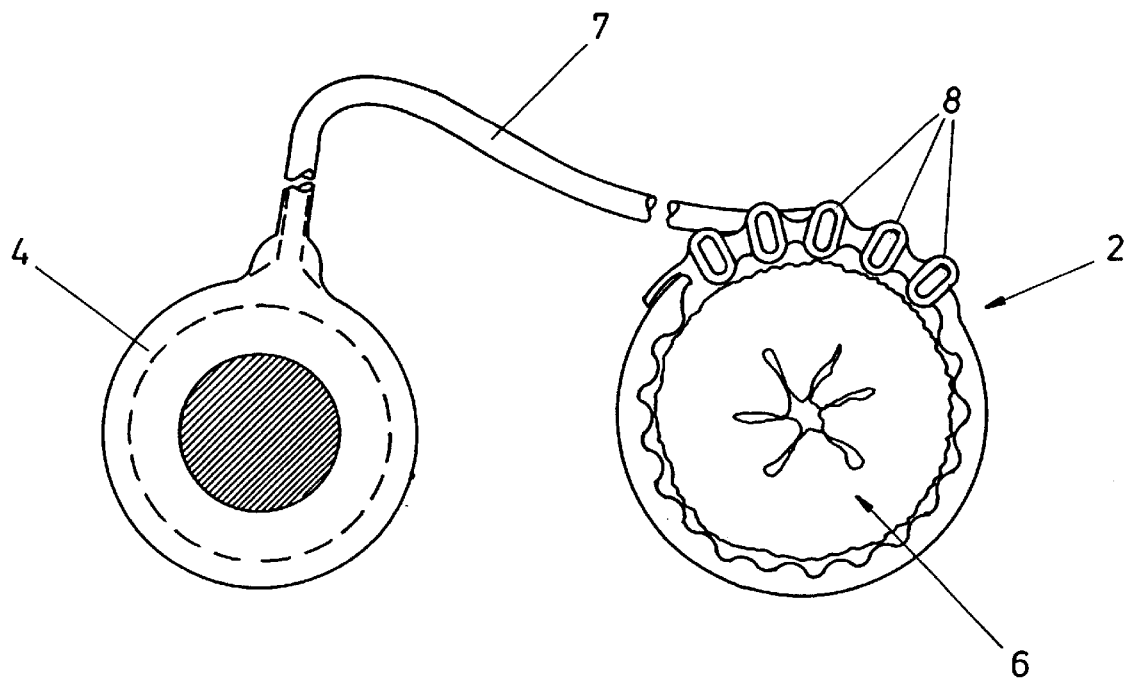
FIG. 1 is an isometric view of the device of the present invention.

FIG. 1 shows a urinary sphincter control device which comprises a multi-chamber cuff 2 which can be positioned around a urethra 6 and an actuator 4. The cuff comprises a plurality of substantially parallel chambers 8 which extend through the cuff in line with the axis of the cuff. Each of the chambers can be inflated by means of hydraulic fluid whose pressure can be adjusted by means of the actuator 4.

The cuff comprises eighteen chambers. The length of the cuff is about 15 mm. The internal perimeter dimension of each of the chambers is about 4 mm. The chambers are in fluid communication with one another to admit pressurised control fluid that is supplied from the actuator 4 through a supply line 7. The chambers are connected to one another by a web 9. The distance between adjacent chambers is about 1.5 mm. Fluid communication between adjacent chambers is provided by a control fluid passage 11 in the webs.

Figure 2:
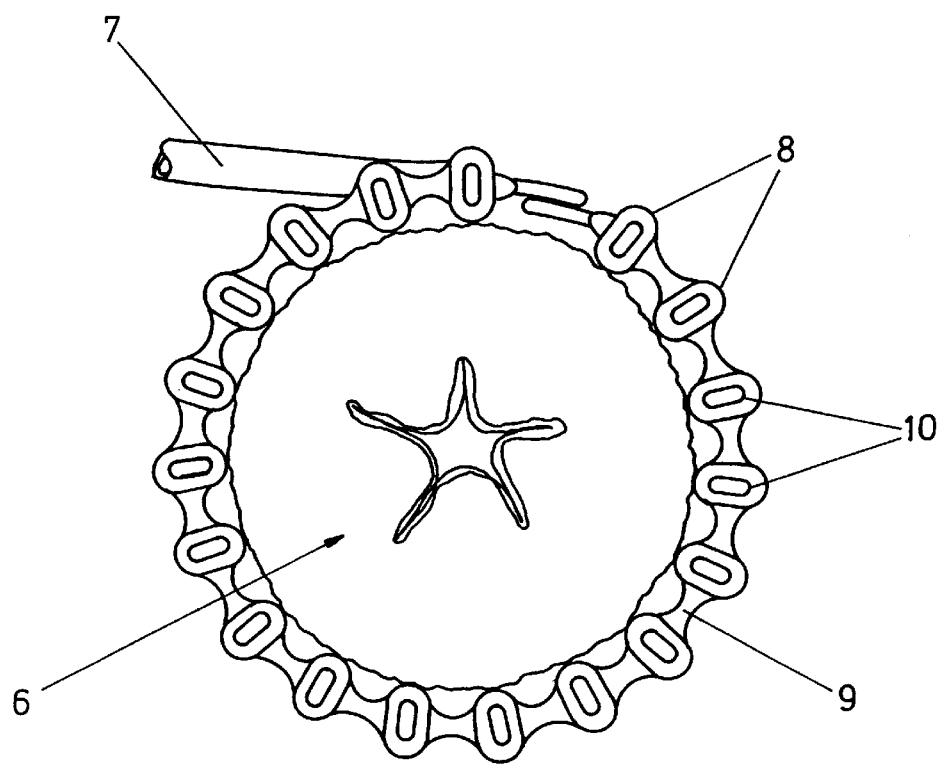
FIG. 2 is a sectional elevation through a cuff component of a device according to the invention, in place around a urethra with the urethra closed against fluid flow.
Figure 3:
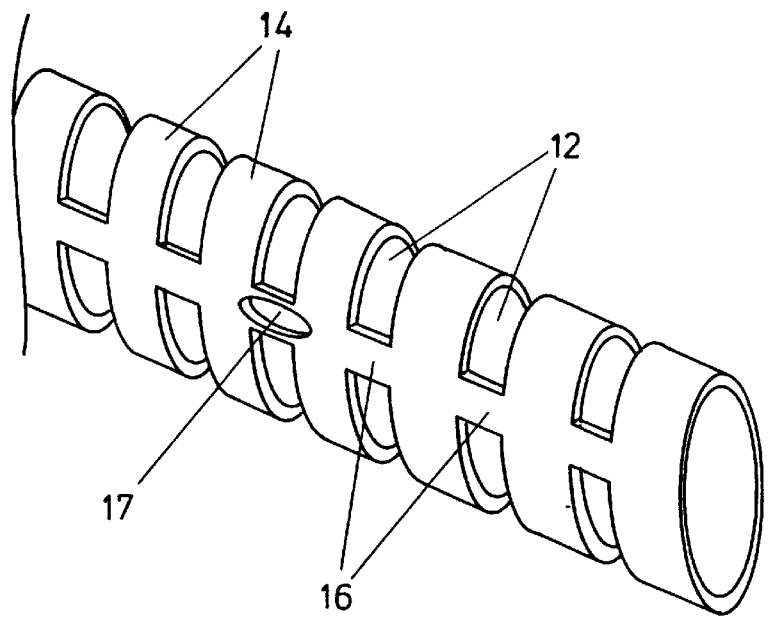
FIG. 3 is an isometric view of a biassing element which can be used in the device of the invention.

As shown in FIG. 2, each of the chambers 8 contains a tubular biasing element 10. The biasing element is formed from a shape memory alloy which consists of 55.8 at. % Ni and 44.2 at. % Ti. The biasing element has a plurality of circumferentially extending slots 12 cut into it so that its structure consists of a plurality of rings 14 that are connected by means of axially extending bars 16. In FIG. 2, the bars are shown as aligned. However, alternative constructions may be employed in which bars between adjacent pairs of rings are not aligned. The slotted structure makes the biasing element flexible. The flexibility of the structure can be selected by appropriate design of the slots including their number, size and location. The element has an opening 17 formed in it for flow of control fluid that is supplied to the chamber from the actuator.

The biasing element is formed by extrusion of a tube of the selected alloy with a wall thickness of about 0.2 mm. Preferably, the wall thickness is at least about 0.08 mm, especially at least about 0.12 mm. The wall thickness will generally be not more than about 0.8 mm, preferably not more than about 0.5 mm, more preferably not more than about 0.4 mm. The slots are formed in the tube by means of a YAG laser cutting device.

The element has shape memory properties imparted to it by a process which includes, for example, one or more thermo- or mechanical working steps. The selection of appropriate steps to ensure that the element exhibits appropriate non-linear superelastic properties when deformed is well established. Preferably, the $A_f$ transformation temperature of the alloy is at least about 0° C., more preferably at least about 5° C. Preferably, the transformation temperature is not more than about 25° C., more preferably not more than about 20° C., for example in the range 5 to 18° C. Preferably, the loading plateau stress of the alloy, measured by deforming a sample of the alloy at a strain rate of $3\%.min^{-1}$ is at least about 300 MPa, more preferably at least about 400 MPa. Preferably, the said loading plateau stress is not more than about 600 MPa, more preferably not more than about 500 MPa.

Figure 4:
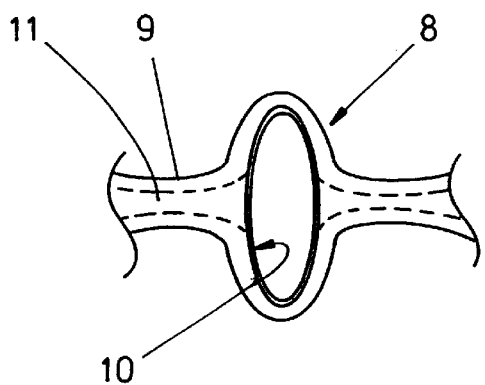
FIG. 4 is a sectional elevation through one of the chambers of the cuff component shown in FIG. 2, with the cuff component in the configuration in which the urethra is closed against flow of fluid.

In its undeformed configuration, the biasing element 10 has a flattened configuration. It is capable of being deformed elastically from this flattened configuration towards a rounded configuration. FIG. 4 shows a biasing element in place within a chamber 8 in the cuff while in its undeformed flattened configuration. The biasing element is arranged with its longitudinal axis aligned with the chamber, and with a urethra when the cuff is positioned for use. The biasing element 10 is oriented within the chamber 8 so that one of its opposite edges 18 is directed inwardly towards the urethra and the other edge is directed away from the urethra. The biasing element is a sliding fit in the chamber so that the chamber is made to adopt the flattened configuration of the biasing element, as can be seen in FIG. 4.

Figure 5:
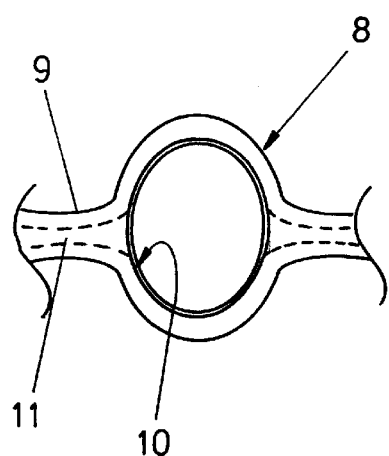
FIG. 5 is a sectional elevation the chamber shown in FIG. 3, with the cuff component in the configuration in which the urethra is open for flow of fluid.

When pressurised control fluid is supplied to the chamber 8 by means of the actuator, through the fluid control passages 11 in the webs 9, the volume of the chamber is made to increase by changing from the flattened configuration shown in FIG. 4 towards the rounded configuration shown in FIG. 5. This involves elastically deforming the biasing element 10 from its flattened configuration. As a result, both the internal diameter of the cuff and its circumference increase, reducing the constriction on the urethra and opening it for fluid flow.

The device is implanted by positioning the cuff around a patient's urethra. The actuator is positioned conveniently so that it can be accessed by the patient for manual actuation, just below the skin.

In its unpressurised condition, the biasing elements 10 cause the chambers 8 to adopt a flattened configuration as shown in FIG. 4. As a result, the internal diameter of the cuff and its circumference are small, and the internally facing longitudinal edges 18 of the biasing element force the walls of the chambers against the urethra to close it against fluid flow.

When pressure is supplied to the chambers 8, their configuration changes from that shown in FIG. 4 to that shown in FIG. 5, so that both the internal diameter of the entire cuff and its circumference increase. This reduces the force which the longitudinal edges exert on the walls of the chambers against the urethra, allowing the urethra to open for fluid flow.

In the embodiment described with reference to FIG. 2, all of the chambers 8 contain biasing elements 10, and all are connected to the actuator in a single array so that they can be inflated together with the control fluid. It can however be preferred for less than all of the chambers to contain biasing elements, for example as shown in FIG. 1. It can also be preferred for the chambers to be connected to the actuator in separate arrays that are spaced apart around the cuff. For example, the inflatable chambers might be arranged in two arrays on opposite sides of the cuff. Separate arrays can be contiguous so that, for example, when there are two arrays, each occupies half of the cuff. Alternatively, separate arrays can be spaced apart around the cuff.

Figure 6:
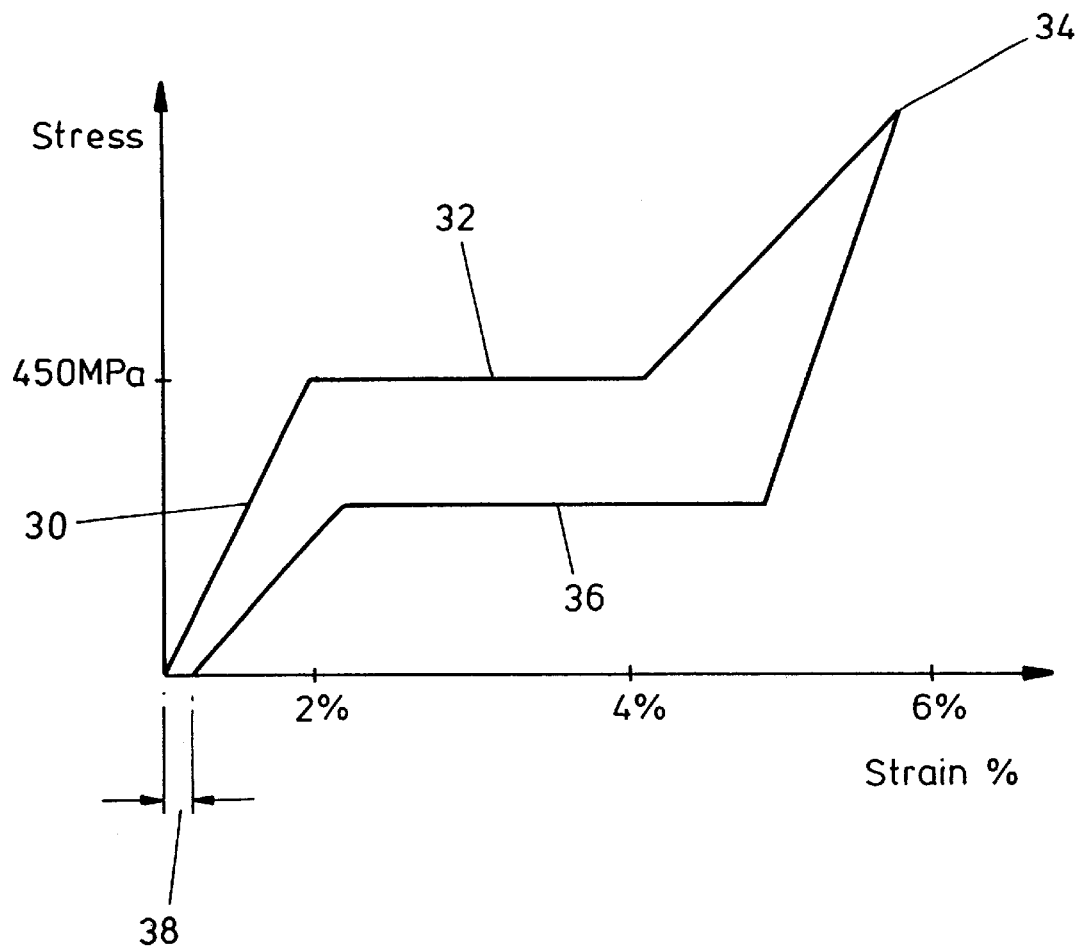
FIG. 6 is a schematic representation of the stress-strain behaviour during deformation of a biassing element made from a shape memory alloy which displays nonlinear superelastic properties.

The nature of the non-linear superelastic properties of the biasing element are illustrated in FIG. 6 which shows the variation of stress with strain as the element is deformed. In an initial deformation phase 30, stress increases approximately linearly with strain, to a strain of about 2% when the stress is about 450 MPa. During subsequent deformation over a strain range of about 2% to about 4%, stress remains substantially constant, This is the so-called loading plateau 32. Subsequent increases in strain are accompanied by an increase in stress to an elastic limit 34. On unloading, initial reductions in stress are accompanied by a corresponding reduction in strain. Over a reduction in strain from about 5% to about 2.5%, stress remains substantially constant. This is the so-called unloading plateau 36. The stress through the unloading plateau is about 60% of that on the loading plateau. At the end of the unloading plateau, reductions in stress are accompanied by approximately linear reductions in strain. Any retained strain 38 at zero stress represents a permanent set of the element.

What is claimed is:

1. A urinary sphincter control device for application to a urethra to control flow of fluid through the urethra, comprising a cuff configured be fitted around the urethra, the cuff comprising a plurality of chambers which are discontinuous around the urethra so that blood is able to flow along the urethra in its wall even when the urethra is closed against fluid flow, which can be inflated to cause the configuration of the cuff to change so as to alter the resistance that is provided by the cuff to flow of fluid through the urethra, and at least one of the chambers containing therein a resiliently deformable biassing element for biassing the chamber configuration towards an uninflated configuration, and wherein the biassing element is formed from a shape memory alloy which exhibits non-linear superelastic properties.

2. A urinary sphincter control device as claimed in claim 1, in which the cuff chambers are arranged so that they extend substantially parallel to the axis of the cuff.

3. A urinary sphincter control device as claimed in claim 2, in which the angle between the axis of the cuff and the axis of the chambers is less than about 20°.

4. A urinary sphincter control device as claimed in claim 1, in which flow of fluid along the urethra is restricted by the cuff when it is in its uninflated configuration, and in which the effective internal perimeter dimension of the cuff is increased when it is in its inflated configuration so that the pressure imposed by the cuff on the urethra is reduced and so that the urethra is opened to flow of fluid therethrough.

5. A urinary sphincter control device as claimed in claim 1, in which the chambers have a generally flattened cross-section when viewed along their axes when uninflated, and in which supply of control fluid to the chamber causes the cross-section of the chambers to become more rounded.

6. A urinary sphincter control device as claimed in claim 5, in which the biassing element has a generally tubular configuration with the axis of the tube extending generally parallel to the axis of the chamber, the biassing element having a generally flattened cross-section when viewed along the axis of the chamber in its uninflated configuration, and in which supply of control fluid to the chamber causes its cross-section to become more rounded.

7. A urinary sphincter control device as claimed in claim 6, in which the biassing element comprises a tube which has a plurality of slots formed in it which extend around at least part of the periphery of the tube.

8. A urinary sphincter control device as claimed in claim 7, in which the slots are arranged in a plane which is generally perpendicular to the axis of the tube.

9. A urinary sphincter control device as claimed in claim 1, in which the cuff comprises an array of the said chambers which extends around the entire periphery of the cuff.

10. A urinary sphincter control device as claimed in claim 9, in which the cuff comprises at least 8 chambers in the said array.

11. A urinary sphincter control device as claimed in claim 1, in which the cuff has at least one array of closely spaced chambers which extends around only part of the periphery of the cuff.

12. A urinary sphincter control device as claimed in claim 11, in which the cuff has at least two of the said arrays of chambers, the arrays being spaced apart around the periphery of the cuff.

13. A urinary sphincter control device for application to a urethra to control flow along the urethra, which comprises
    (a) a cuff configured to be fitted around the urethra and configured to be inflated to cause the configuration of the device to change between an uninflated configuration in which flow of fluid along the urethra is restricted and an inflated configuration in which fluid is able to flow along the urethra, and
    (b) an element for biassing the device towards the uninflated configuration. the element is formed from a shape memory alloy which has been treated so that it exhibits non-linear superelastic properties at body temperature, allowing it to be deformed by inflation of the cuff and to recover elastically when the cuff deflates.

14. A urinary sphincter control device as claimed in claim 13, in which the cuff comprises a plurality of chambers configured be inflated by supply of pressurised control fluid thereto to cause the configuration of the cuff to change so as to alter the resistance that is provided by the cuff to flow of fluid along the urethra.

15. A urinary sphincter control device as claimed in claim 14, in which the biassing element is located in one of the chambers.

16. A urinary sphincter control device as claimed in claim 15, in which the biassing element has a generally tubular configuration with the axis of the tube extending generally parallel to the axis of the chamber in which it is located, the biassing element having a generally flattened cross-section when viewed along the axis of the chamber in its uninflated configuration, and in which supply of control fluid to the chamber causes its cross-section to become more rounded.

* * * * *